United States Patent
Aggarwal et al.

(10) Patent No.: US 6,617,178 B1
(45) Date of Patent: Sep. 9, 2003

(54) TEST SYSTEM FOR FERROELECTRIC MATERIALS AND NOBLE METAL ELECTRODES IN SEMICONDUCTOR CAPACITORS

(75) Inventors: Sanjeev Aggarwal, Plano, TX (US); Kaushal K. Singh, Santa Clara, CA (US)

(73) Assignees: Agilent Technologies, Inc, Palo Alto, CA (US); Texas Instruments, Dallas, TX (US); Applied Materials, Santa Clara, CA (US)

( * ) Notice: Subject to any disclaimer, the term of this patent is extended or adjusted under 35 U.S.C. 154(b) by 0 days.

(21) Appl. No.: 10/190,402

(22) Filed: Jul. 2, 2002

(51) Int. Cl.$^7$ ............... H01L 21/00; H01L 21/66
(52) U.S. Cl. ............... 438/16; 438/14; 438/3
(58) Field of Search ............... 438/3, 14, 16

(56) References Cited

U.S. PATENT DOCUMENTS

| | | | |
|---|---|---|---|
| 5,483,568 A | * | 1/1996 | Yano et al. |
| 6,096,434 A | * | 8/2000 | Yano et al. |
| 6,127,218 A | | 10/2000 | Kang |
| 6,144,060 A | * | 11/2000 | Park et al. |
| 6,328,433 B1 | * | 12/2001 | Moriya et al. |
| 6,387,712 B1 | * | 5/2002 | Yano et al. |
| 6,494,566 B1 | * | 12/2002 | Kishino et al. |
| 2003/0021732 A1 | * | 1/2003 | Tungare et al. |

\* cited by examiner

Primary Examiner—John F. Niebling
Assistant Examiner—Stanetta Isaac

(57) ABSTRACT

A method is provided for ferroelectric layer testing. An adhesion layer is deposited over a semiconductor substrate to be of a phase pure material lacking a first material. A lower electrode is deposited over the adhesion layer and a ferroelectric layer is deposited over the lower electrode. The ferroelectic layer contains the first material. The ferroelectric layer is x-rayed and the x-ray fluorescence from the ferroelectric layer is detected for characterizing the ferroelectric layer.

20 Claims, 1 Drawing Sheet

TEST SYSTEM FOR FERROELECTRIC MATERIALS AND NOBLE METAL ELECTRODES IN SEMICONDUCTOR CAPACITORS

BACKGROUND

1. Technical Field

The present invention relates generally to testing semiconductor material combinations and more specifically to test ferroelectric

2. Background Art

As the electronic industry develops, several trends drive the development of new technologies. First, people want smaller and smaller products, which require less frequent replacement of batteries, such as cell phones, personal sound systems, digital cameras, etc. Second, in addition to being smaller and more portable, these products are required to have more computational power and more memory storage capability. Third, these devices are expected to maintain information, pictures, etc. even when the batteries die.

Non-volatile memories such as electrically erasable programmable read only memories (EEPROMs), and flash EEPROMs are used in such products because they can maintain data without power. These memories include arrays of memory cells, in which each memory cell includes a memory cell capacitor and a memory cell access transistor.

A new type of non-volatile memory is currently being developed which is based on ferroelectric materials and is called a ferroelectric memory or FeRAM. At this point, there are many different ferroelectric materials and a vast number of different formulations of ferroelectric materials that are being investigated. Since a memory cell must maintain data without power, the memory cell's material must be capable of holding the electrical charge, which represents one bit of data. Thus, one of the key characteristics of the ferroelectric materials, which must be determined and improved, is its charge retention capability or capacitance.

The capacitance of a given capacitor is a function of the dielectric constant of the capacitor dielectric, the effective area of the capacitor electrode, and the thickness of the capacitor dielectric layer. Essentially, decreasing the thickness of the dielectric layer, increasing the effective area of the capacitor electrodes, and increasing the dielectric constant of the capacitor dielectric can increase the capacitance. For smaller products, it is desirable to have a small thickness and a high capacitance.

Decreasing the thickness of a capacitor dielectric layer below 100 Å generally reduces the reliability of the capacitor, because Fowler-Nordheim hot electron injection may create holes through the thin dielectric layers.

Increasing the effective area of the capacitor electrode generally results in a more complicated and expensive capacitor structure. For example, three dimensional capacitor structures such as stack-type structures and trench-type structures have been applied to 4 MB DRAMs, but these structures are difficult to apply to 16 MB or 64 MB DRAMs. A stack-type capacitor may have a relatively steep step due to the height of the stack-type capacitor over the memory cell transistor and trench-type capacitors may have leakage currents between the trenches when scaled down to the size required for a 64 MB DRAM.

Increasing the dielectric constant of the capacitor dielectric requires the use of relatively high dielectric constant materials. Currently, silicon dioxide ($SiO_2$) with a dielectric constant around ten is used. Higher dielectric constant materials, such as yttria ($Y_2O_3$), tantalum oxide ($Ta_2O_5$), and titanium oxide ($TiO_2$), have been tried. In addition, ferroelectric materials which have even higher dielectric constants, such as PZT ($PbZr_xTi_{(1-x)}O_3$), BST ($Ba_xSr_{(1-x)}TiO_3$), or STO ($SrTiO_3$), have been used to provide a new family of memories called ferroelectric random access memories (FRAMs).

Materials such as PZT, $SrBi_2Ta_2O_9$ and $(BiLa)_4Ti_3O_{12}$, $Bi_3Ti_4O_{12}$ are ferroelectric at room temperature and become paraelectric only at temperatures as high as 450C. As such they exhibit a hysteresis in their charge-field response and have a remnant charge even at zero field at room temperature. Further, either a positive or a negative charge can be stored depending on the applied field thus naturally offering two states representing "1" or "0" data bits. Thus, these materials make good non-volatile memories.

BST and STO are ferroelectric materials but only at or just below room temperature. At room temperature they are paraelectric materials, i.e. linear dielectrics, which makes them appropriate for dynamic random access memories. The idea behind trying to integrate BST or STO in memories was to take advantage of their high dielectric constant to thereby enable scaling to lower equivalent oxide thicknesses.

Unfortunately, it was found that trying to take advantage of the high dielectric constant of STO and BST ferroelectrics by scaling to lower equivalent oxide thickness resulted in other problems. Capacitors using ferroelectric materials would be subject to leakage currents, which would discharge the capacitors and effectively decrease the dielectric constant of the ferroelectric materials. For example, BST would have a dielectric constant around 400 to 500 but the dielectric constant would be reduced to around 20 to 50 in a capacitor.

After investigation, it was discovered that the electrodes on both sides of the ferroelectric material were the sources of the problem. The interface between each electrode and the ferroelectric material has an interfacial capacitance, which acts in parallel with the capacitance of the ferroelectric material. Where the interfacial capacitance is low, the capacitance of the combination with the ferroelectric material will be low despite having a high dielectric constant ferroelectric material.

Fortunately, non-volatile memories based on materials such as PZT, SBT, BLT and BiTi—O that are ferroelectric at room temperature do not have to be scaled down to 10 nm thickness range. Typical thickness used is of the order of 100 nm. As such the interfacial properties are not dominant. Furthermore, it has been discovered that the endurance of the capacitors can be improved by the use of a combination of the ferroelectric material and a noble metal electrode of a noble metal such as platinum (Pt) or iridium (Ir) or their oxides and perovskite electrodes such as $LaNiO_3$ and $SrRuO_3$. However, the degree of improvement could only be measured by manufacturing complete devices with different ferroelectric materials and noble metal electrodes, and testing each one of them. With the vast number of different chemical combinations of the ferroelectric layer possible, this process of characterizing the combinations becomes extremely expensive and time consuming.

It has also been discovered that an adhesion layer is required between the bottom electrode (BE) and the substrate since invariably the lower electrode delaminates at the TEOS/BE interface when trying to delineate capacitors by etching but there has been no way of characterizing these combinations also.

It has been found that for lower size substrates, 2 to 4 inches, $LaAlO_3$ or $Al_2O_3$ substrates can be used for test structures, but 8 inch substrates cannot be used due to prohibitive costs or the impossibility of preparing such substrates.

Solutions to this problem has been long sought, but have long eluded those skilled in the art.

DISCLOSURE OF THE INVENTION

The present invention provides a method for ferroelectric layer testing. An adhesion layer is deposited over a semiconductor substrate to be of a phase pure material lacking a first material. A lower electrode is deposited over the adhesion layer and a ferroelectric layer is deposited over the lower electrode. The ferroelectic layer contains the first material. The ferroelectric layer is x-rayed and the x-ray fluorescence from the ferroelectric layer is detected for characterizing the ferroelectric layer. The method provides an inexpensive and quick method for characterizing vast numbers of different combinations of the ferroelectric layer.

Certain embodiments of the invention have other advantages in addition to or in place of those mentioned above. The advantages will become apparent to those skilled in the art from a reading of the following detailed description when taken with reference to the accompanying drawings.

BEST MODE FOR CARRYING OUT THE INVENTION

Figure 1:
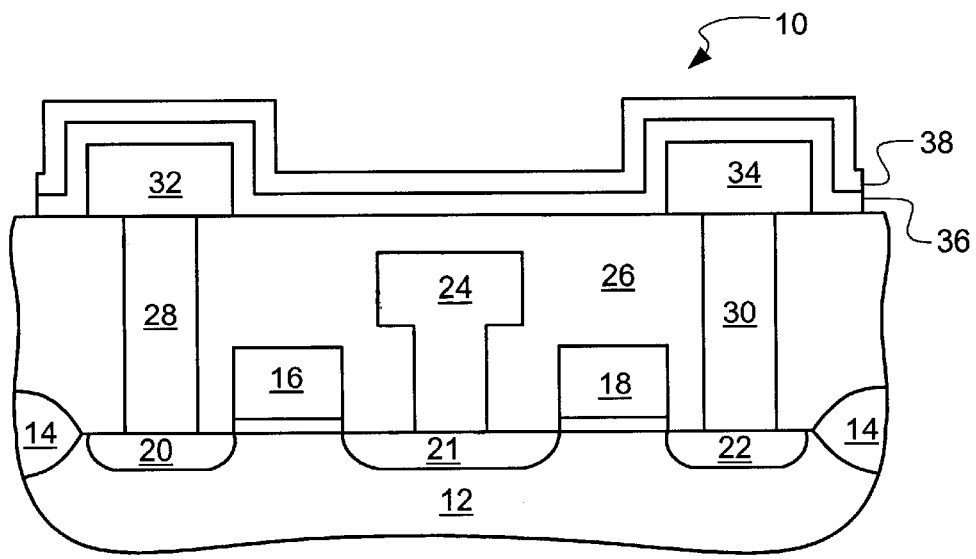
FIG. 1 is a cross-sectional view of a three dimensional ferroelectric memory integrated circuit.

Referring now to FIG. 1, therein is shown is a cross-sectional view of a three-dimensional ferroelectric memory integrated circuit 10 using a ferroelectric layer formed using materials tested by the method of the present invention. A semiconductor substrate 12 has a shallow trench isolation oxide layer 14, gates and gate dielectrics 16 and 18, and source/drain regions 20–22. A bit line 24 is formed in an interlayer dielectric (ILD) layer 26 in contact with one source/drain region 21, and buried contacts 28 and 30 are formed through the ILD layer 26 and are respectively in contact with source/drain regions 20 and 22.

Lower electrodes 32 and 34 are formed in contact with respective buried contacts 28 and 30. A ferroelectric layer 36 is deposited over the buried contacts 28 and 30. And, an upper electrode 38 is deposited over the ferroelectric layer 36. Basically, the gates and gate dielectrics 16 and 18, and the source/drain regions 20–22 form the transistors of the ferroelectric memory integrated circuit 10 while the lower electrodes 32 and 34, the ferroelectric layer 36, and the upper electrode 38 form the memory capacitor.

The lower electrodes 32 and 34 and the upper electrode 38 are formed from a noble metal material or compound such as Pt, Ir, Ru, $IrO_2$, or $RuO_2$. The ferroelectric layer 36 is generally deposited using a metal organic chemical vapor deposition (MOCVD) technique. The ferroelectric layer 36 can be of materials such as PZT ($PbZr_xTi_{(1-x)}O_3$), BST ($Ba_xSr_{(1-x)}TiO_3$), STO ($SrTiO_3$), or $Bi_4Ti_3O_{12}$. It should be noted that all the ferroelectric layers designated contain titanium, and although they are designated as ferroelectric layers, they do not contain iron.

Figure 2:
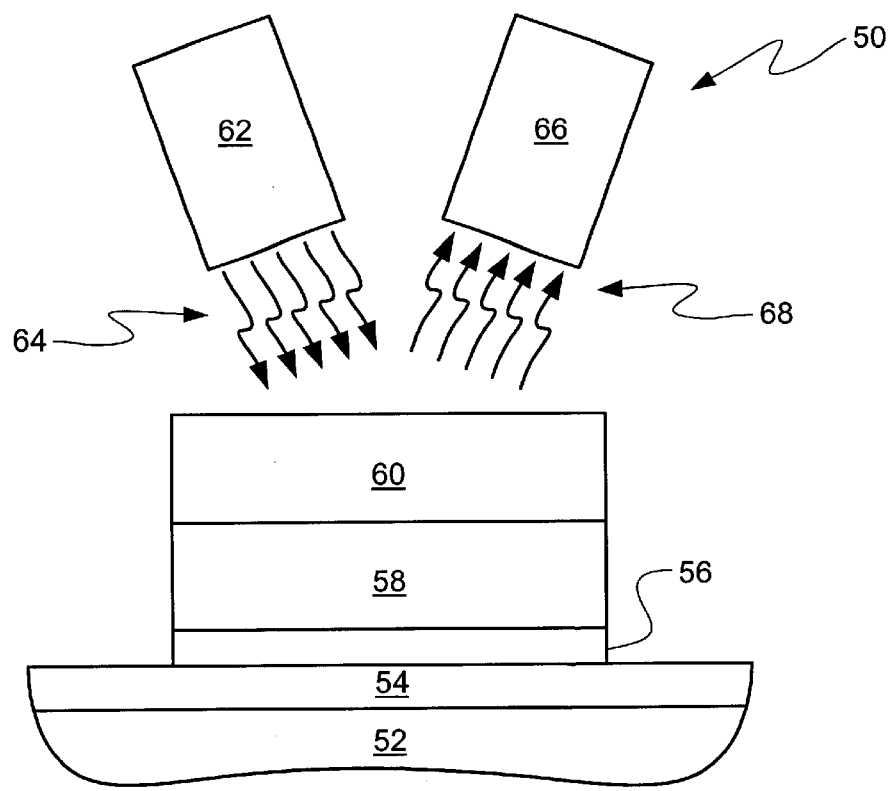
FIG. 2 is a ferroelectric layer test system.

Referring now to FIG. 2, therein is shown a ferroelectric layer test system 50. The test system 50 includes a test structure, which includes an semiconductor substrate 52 having an oxide deposition 54. The oxide deposition 54 can be of a material such as plasma enhanced-tetraethyl orthosilicate (PETEOS), a thermal oxide, and LPCVD TEOS.

Deposited over the oxide deposition 54 is adhesion layer 56 in accordance with the present invention, which will be described more fully later.

Above the adhesion layer 56 is a lower electrode 58 of a noble metal material or compound such as Pt, Ir, Ru, $IrO_2$, or $RuO_2$. Above the lower electrode 58 is a ferroelectric layer 60 of titanium containing materials such as PZT ($PbZr_xTi_{(1-x)}O_3$), BST ($Ba_xSr_{(1-x)}TiO_3$), STO ($SrTiO_3$), or $Bi_4Ti_3O_{12}$. The test structure does not require an upper electrode.

The test system 50 further includes an x-ray generator 62 for generating x-rays 64 at the ferroelectric layer 60 and an x-ray fluorescence detector 66 for measuring the fluorescence 68 of the ferroelectric layer 60.

In the past, an adhesion layer was required for depositing the lower electrode on an oxide deposition. Traditionally, the lower electrode would be a noble metal such as platinum or iridium and the adhesion layer would be titanium or a titanium aluminum nitride. However, two major problems were discovered when this type of structure was used for characterizing ferroelectric layers.

First, the ferroelectric layers were not uniform in thickness. After investigation, it was discovered that oxidation was occurring under the lower electrode. This was traced to the titanium component of the adhesion layer, which was found to be susceptible to oxidation during deposition of the ferroelectric layer over the lower electrode. This oxidation was found to cause roughness of the adhesion layer, which translated to uneven thickness of the lower electrode and, consequently, of the ferroelectric layer.

Second, it was discovered that the oxidation would cause peeling of the lower electrode from the oxide deposition.

Third, it was discovered that x-ray fluorescence testing provided erroneous characterizations. X-ray fluorescence is used to characterize the composition and thickness of the deposited PZT film. This measurement is based on the intensity of the components lead, zirconium, and titanium, which are calibrated to known standards. If the adhesion layer has titanium, the titanium intensity would be higher as compared to the PZT film. Therefore, the film properties would be incorrectly measured.

When attempting to replace the titanium with aluminum (Al), aluminum nitride (AlN), or aluminum oxide ($Al_2O_3$), it was found that there were still problems with testing because there would be adhesion issues with excess aluminum oxidizing or reacting with lower electrode and/or PZT leading to adhesion problems.

It was discovered that in order to avoid the interference, it was necessary to deposit a phase pure aluminum nitride layer or phase pure aluminum oxide layer with a refractive index of about 2.0. As used herein, the term "phase pure" layer refers to a layer in which x-ray diffraction exhibits only peaks for one crystal structure. For example, a two phase material of PZT could show peaks for a pyrochlore phase (Pb—Ti—O) and perovskite PZT. The perovskite PZT is the desired ferroelectric phase and the pyrochlore phase is paralectric and highly leaky.

Also, it was discovered that the stress tensile needs to be over about 800 MPa to avoid peeling and the rms roughness needs to be under about 3 nm to provide uniformity of thickness of the ferroelectric layer.

To deposit the phase pure aluminum nitride layer with a refractive index of about 2.0, it was discovered that a reactive sputtering with a pulsed DC power source could be used with the following preferred parameters: argon at about 20 sccm, heater argon at about 15 sccm, nitrogen at 99 sccm; heater temperature of about 400° C.; power between 3000 and 5000 watts; frequencies from 75 to 200 kHz; pulse widths from 500 to 2700 ns; and prevention of arcing during deposition.

The above solved the problems associated with titanium and titanium based adhesion layers and provided the pure phase layer necessary for the adhesion film 56 of the present invention.

While the invention has been described in conjunction with a specific best mode, it is to be understood that many alternatives, modifications, and variations will be apparent to those skilled in the art in light of the aforegoing description. Accordingly, it is intended to embrace all such alternatives, modifications, and variations which fall within the spirit and scope of the included claims. All matters hither-to-fore set forth herein or shown in the accompanying drawings are to be interpreted in an illustrative and non-limiting sense.

The invention claimed is:

1. A method for ferroelectric layer testing comprising:
   depositing an adhesion layer over a semiconductor substrate, the adhesion layer deposited to be of a phase pure material lacking a first material;
   depositing a lower electrode over the adhesion layer;
   depositing a ferroelectric layer over the lower electrode, the ferroelectic layer containing the first material;
   x-raying the ferroelectric layer; and
   detecting the x-ray fluorescence from the ferroelectric layer for characterizing the ferroelectric layer.

2. The method as claimed in claim 1 wherein depositing the adhesion layer deposits an aluminum compound.

3. The method as claimed in claim 1 wherein depositing the adhesion layer deposits a material having a refractive index of about 2.0.

4. The method as claimed in claim 1 wherein depositing the adhesion layer deposits a material having a stress tensile over about 800 MPa.

5. The method as claimed in claim 1 wherein depositing the ferroelectric layer causes the adhesion layer to have a rms roughness under about 3 nm.

6. The method as claimed in claim 1 wherein depositing the adhesion layer deposits a material using a reactive sputtering with a pulsed DC power source.

7. The method as claimed in claim 1 wherein depositing the adhesion layer deposits a material using reactive sputtering with argon at about 20 sccm, argon-hydrogen at about 15 sccm, and nitrogen at 99 sccm.

8. The method as claimed in claim 1 wherein depositing the adhesion layer deposits a material using reactive sputtering with a heater temperature of about 400° C.

9. The method as claimed in claim 1 wherein depositing the adhesion layer deposits a material using reactive sputtering with power between 3000 and 5000 watts, frequencies from 75 to 200 kHz, and no arcing.

10. The method as claimed in claim 1 wherein depositing the adhesion layer deposits a material using reactive sputtering with pulse widths from 500 to 2700 ns.

11. A method for ferroelectric layer testing comprising:
    providing a silicon substrate;
    depositing an oxide layer over the silicon substrate;
    depositing an aluminum-based adhesion layer over the oxide layer, the aluminum-based adhesion layer deposited to be of a phase pure material lacking a first material;
    depositing a lower electrode over the aluminum-based adhesion layer;
    depositing a ferroelectric layer over the lower electrode, the ferroelectic layer containing the first material;
    x-raying the ferroelectric layer; and
    detecting the x-ray fluorescence from the ferroelectric layer for characterizing the ferroelectric layer.

12. The method as claimed in claim 11 wherein depositing the aluminum-based adhesion layer deposits a material selected from a group consisting of aluminum nitride and aluminum oxide.

13. The method as claimed in claim 11 wherein depositing the aluminum-based adhesion layer deposits an aluminum compound having a refractive index of about 2.0.

14. The method as claimed in claim 11 wherein depositing the aluminum-based adhesion layer deposits an aluminum compound having a stress tensile over about 800 MPa.

15. The method as claimed in claim 11 wherein depositing the ferroelectric layer causes the aluminum-based adhesion layer to have a rms roughness under about 3 nm.

16. The method as claimed in claim 11 wherein depositing the aluminum-based adhesion layer deposits an aluminum compound using a reactive sputtering with a pulsed DC power source.

17. The method as claimed in claim 11 wherein depositing the aluminum-based adhesion layer deposits an aluminum compound using reactive sputtering with argon at about 20 sccm, argon-hydrogen at about 15 sccm, and nitrogen at 99 sccm.

18. The method as claimed in claim 11 wherein depositing the aluminum-based adhesion layer deposits an aluminum compound using reactive sputtering with a heater temperature of about 400° C.

19. The method as claimed in claim 11 wherein depositing the aluminum-based adhesion layer deposits an aluminum compound using reactive sputtering with power between 3000 and 5000 watts, frequencies from 75 to 200 kHz, and no arcing.

20. The method as claimed in claim 11 wherein depositing the aluminum-based adhesion layer deposits an aluminum compound using reactive sputtering with pulse widths from 500 to 2700 ns and no arcing.

* * * * *